(12) United States Patent
Goodman et al.

(10) Patent No.: US 6,341,518 B1
(45) Date of Patent: Jan. 29, 2002

(54) ULTRASONIC STANDARD

(75) Inventors: Mark A. Goodman, Cortlandt Manor, NY (US); Betty J. R. Chavez, Arvada, CO (US)

(73) Assignee: U.E Systems, Inc., Elmsford, NY (US)

( * ) Notice: Subject to any disclaimer, the term of this patent is extended or adjusted under 35 U.S.C. 154(b) by 0 days.

(21) Appl. No.: 09/459,307

(22) Filed: Dec. 10, 1999

(51) Int. Cl.$^7$ ............................................. G01N 29/00

(52) U.S. Cl. ........................................ 73/1.86; 181/142

(58) Field of Search ............................ 73/1.82, 1.86; 181/142; 367/13

(56) References Cited

U.S. PATENT DOCUMENTS

| | | | |
|---|---|---|---|
| 408,635 A | 8/1889 | Sommer | 446/168 |
| 1,586,769 A | 6/1926 | Askin | 84/403 |
| 2,144,857 A | 1/1939 | Schultz | 368/93 |
| 2,375,568 A | 5/1945 | McAuliffe | 368/93 |
| 2,383,305 A | 8/1945 | Greene | 446/143 |
| 2,504,456 A | 4/1950 | Rundell | 84/404 |
| 2,504,457 A | 4/1950 | Rundell | 84/404 |
| 2,868,923 A | 1/1959 | Epstein | 335/63 |
| 3,002,313 A | 10/1961 | Hutchinson | 446/9 |
| 3,677,061 A | 7/1972 | Visser | 73/1.83 |
| 3,698,128 A | 10/1972 | Moeser | 446/49 |
| 3,903,988 A * | 9/1975 | Hermsen et al. | 181/142 |
| 3,906,884 A | 9/1975 | Gould | 114/244 |
| 3,924,444 A | 12/1975 | Heyman et al. | 73/1.85 |
| 3,935,702 A | 2/1976 | Tamada | 368/93 |
| 3,938,315 A | 2/1976 | Von Kemenczky | 368/94 |
| 4,064,735 A * | 12/1977 | Hutchison et al. | 73/1.82 |
| 4,128,949 A | 12/1978 | Marason, Jr. et al. | 434/304 |
| 4,201,093 A | 5/1980 | Logan | 73/618 |
| 4,284,164 A | 8/1981 | Airhart | 181/117 |
| 4,284,165 A | 8/1981 | Airhart et al. | 181/119 |
| 4,287,680 A | 9/1981 | Allen et al. | 446/192 |
| 4,306,485 A | 12/1981 | Rudkin | 84/402 |
| 4,393,711 A | 7/1983 | Lapides | 73/592 |
| 4,484,657 A | 11/1984 | Barta | 181/121 |
| 4,545,251 A | 10/1985 | Uchida et al. | 73/631 |
| 4,659,224 A | 4/1987 | Monchalin | 356/352 |
| 4,759,253 A | 7/1988 | Härle et al. | 84/484 |
| 4,901,617 A | 2/1990 | Malone et al. | 84/402 |
| 4,961,181 A | 10/1990 | Elliott | 367/142 |
| 4,991,426 A | 2/1991 | Evans | 73/40 |

(List continued on next page.)

FOREIGN PATENT DOCUMENTS

| | | | |
|---|---|---|---|
| EP | 276407 A2 | 8/1988 | 84/402 |
| JP | 59-67427 * | 4/1984 | G01N/29/00 |
| RU | 1627875 A2 * | 2/1991 | 73/1.82 |

OTHER PUBLICATIONS

ASTM Committee, Jun., 1994, pp. 386–391, *Standard Guide for Determining the Reproducibility of Acoustic Emission Sensor Response*.

ASTM Committee, Feb., 1997, pp. 442–424, *Standard Test Method for Leaks Using Ultrasonics*.

*Primary Examiner*—Thomas P. Noland
(74) *Attorney, Agent, or Firm*—Darby & Darby

(57) ABSTRACT

The invention provides a device that generates predictable and reproducible sounds. The device according to the invention serves as a standard to calibrate ultrasonic measuring equipment through either a gaseous medium or a solid medium. The device according to the invention is similar in basic shape to an hourglass or venturi (e.g., a sand-type egg-timer), but instead of using fine particles, such as sand, the device includes identical media particles (e.g., marbles, balls, beads, etc.) which drop from an upper chamber to a lower one. The media particles are pre-sorted so that those sealed within the hourglass structure are uniform. An impingement post (e.g., a bell or sounding plate) is positioned in the path of the falling media particles so that each will hit the sounding plate, resulting in a reverberating sound. The impingement post is cantilevered and supported from a side of a chamber of the hour glass structure.

8 Claims, 6 Drawing Sheets

U.S. PATENT DOCUMENTS

| | | | |
|---|---|---|---|
| 5,163,027 A | 11/1992 | Miller et al. | 367/13 |
| 5,212,331 A | 5/1993 | Waldo | 84/404 |
| 5,445,029 A | 8/1995 | Falsetti et al. | 73/609 |
| 5,505,114 A | 4/1996 | Lawson | 84/404 |
| 5,569,867 A | 10/1996 | Levine | 84/470 R |
| 5,864,517 A | 1/1999 | Hinkey et al. | 367/145 |

* cited by examiner

ULTRASONIC STANDARD

FIELD OF THE INVENTION

The invention relates to the field of acoustic measurement and calibration and, more particularly to a standard and device useful in testing and calibrating ultrasonic equipment and generating predictable and reproducible sounds.

BACKGROUND OF THE INVENTION

A convenient way to test the performance of acoustic equipment is to compare its acoustic emission response to an acoustic source emitting uniformly repeatable sound waves. The comparison is dependent on the acoustic source being able to reproduce sounds reliably and accurately. The acoustic source then serves as an acoustic measurement or calibration standard against which comparisons are made. Repeatable acoustic sounds are generated according to a method known in the art, by carefully breaking a Hsu pencil lead against a test block. The use of a Hsu pencil in generating repeatable sound waves is described in ASTM E976-94, "Standard Guide for Determining the Reproducibility of Acoustic Emission Sensor Response," pp. 388–390, which is incorporated by reference herein. When the lead of the Hsu pencil breaks, there is a sudden release of the stress on the surface of the test block where the lead is touching. The stress release generates an acoustic wave. In generating reproducible, uniform sound waves, care is taken to always break the same length of the same type of lead, and to break the lead at the same spot on the test block with the same angle and orientation of the Hsu pencil.

There are disadvantages inherent in the conventional method using a Hsu pencil for generating repeatable sounds. Great care and effort must be expended to ensure uniformity in the breaking of the Hsu pencil in order to reliably produce repeatable sounds. Additional devices, such as a Nielsen shoe (as shown in ASTM E976-94 "Standard Guide for Determining the Reproducibility of Acoustic Emission Sensor Response", p. 390), are required to achieve that uniformity. Furthermore, once a Hsu pencil is broken to produce a sound, it is no longer reusable.

Calibration standards, and devices therefor, are useful in calibrating ultrasonic instruments used in locating and estimating measurements of gas leakage. Exemplary methods in the art for measuring gas leakage using airborne ultrasonic techniques are described in ASTM E 1002-96, "Standard Test Method for Leaks Using Ultrasonics," pp. 422–424, which is also incorporated by reference herein.

FIG. 1 is a block diagram illustrating a prior art ultrasonic airborne calibration standard for gas leakage. Airborne ultrasound is a pressure wave or longitudinal wave that travels through air. It is produced by either turbulent flow or a vibrating surface. Referring to FIG. 1, there is shown a nitrogen gas supply 11 and a regulator 13 for regulating the gas flow from the nitrogen gas supply 11. The nitrogen gas supply 11 is a pressurized gas source that creates the equivalent of a nitrogen gas leak through an orifice 15. A sound absorbing barrier 17 is selectively placed in front of the orifice 15 to intercept the pressure wave and stop it or removed to allow a uniform wave to be received by air probe 19. Since the wave is uniform because of the regulator, the apparatus forms a standard for gas leakage, which can be used to calibrate probe 19.

FIG. 2 is a flow diagram illustrating the operation of a prior art ultrasonic calibration method for measuring gas leakage using the equipment shown in FIG. 1. Referring to FIG. 2 (in conjunction with FIG. 1), the regulator 13 regulates the gas flow from nitrogen gas supply 1 to a leak standard, e.g., $4.9 \times 10^5$ mol/s (1.1 std. $cm^3$/s at 0° C.) ±5% (step 21). The size of the orifice 15 of the nitrogen gas supply 11 is approximately 0.2 mm (0.008 inches). Since the calibration is conducted in the airborne mode for ultrasound received in a gaseous medium, the air probe 19 is positioned at a distance D1 of 10 meters (±0.1 m) from the orifice 15 (step 23). In step 25, the air probe 19 and the orifice 15 are aligned to obtain peak acoustic response. The flow rate of the gas emitted from the nitrogen gas supply 11 is scaled back 50% of the full scale (±5%). The sound absorbing barrier 17 is placed in front of the orifice 15 blocking out the calibrated gas leak (step 27). The meter reading of the flow rate of the gas being emitted from the nitrogen gas supply 11 is checked to see if it is equal to zero, that is, no audible signal detected (step 29). This calibration process is repeated for each level used in detecting and measuring gas leakage (step 28).

Application of the methodology described in FIGS. 1 and 2 has become impractical today since many industrial environments do not have the space for such a great testing distance (e.g., D1=10 m) with no competing ultrasound. Further, the long testing distance results in low acoustic sensitivity, which has a negative impact on the accuracy of the ultrasonic calibration. Also, in general calibration devices in the art can perform ultrasonic calibration in the airborne mode only, but not in the structure-borne mode for ultrasound received through a solid medium.

A reliable, easy-to-use methodology and device therefor are thus needed for ultrasonic calibration which overcome the problems in the prior art. There is a further need in the art for an ultrasonic calibration method and device for both the airborne mode and the structure-borne mode.

SUMMARY OF THE INVENTION

The present invention relates to a device that generates predictable and reproducible sounds. The device according to the invention serves as a standard to calibrate ultrasonic measuring equipment through either a gaseous medium or a solid medium.

In an exemplary embodiment, the acoustic calibration device according to the invention is similar in basic shape to an hourglass or venturi (e.g., a sand-type egg-timer), but instead of using fine particles, such as sand, the device includes uniform media particles (e.g., marbles, balls, beads, etc.) which drop from an upper chamber to a lower one. The upper chamber is connected to the lower chamber, with a neck disposed therebetween. The media particles are presorted so that those sealed within the hourglass structure are of uniform size. An impingement post (e.g., a bell or sounding plate) is positioned in the path of the falling media particles so that each will hit the sounding plate, resulting in a reverberating sound. The neck allows the passage of only a controlled number of the media particles per unit of time. The impingement post is cantilevered and supported through a connection to the hour glass structure.

The device according to the invention is advantageous over the prior art because it is easy to use and carry, and reliably provides a uniform acoustic output of repeatable sounds without the need for an external energy source. The device according to the invention does not require a large testing space nor additional devices aiding the ultrasonic calibration process. The invention is further advantageous over the prior art in that the device according to the invention can be used for ultrasonic calibration in both the airborne mode and the structure-borne mode.

BRIEF DESCRIPTION OF THE DRAWINGS

These and other features, aspects, and advantages of the invention will become readily apparent with reference to the following detailed description of a presently preferred, but nonetheless illustrative embodiment, when read in conjunction with the accompanying drawings, in which like reference designations represent like features throughout the enumerated Figures. The drawings referred to herein will be understood as not being drawn to scale, except if specifically noted, the emphasis instead being placed upon illustrating the principles of the invention. In the accompanying drawings.

DETAILED DESCRIPTION OF THE PREFERRED EMBODIMENTS

Figure 3:
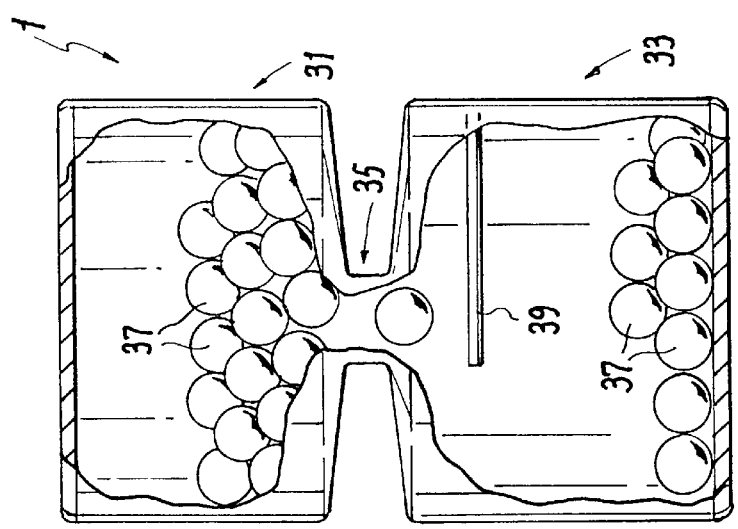
FIG. 3 is a diagram illustrating an embodiment of the acoustic calibration device according to the invention.

FIG. 3 is a diagram that illustrates an acoustic calibration device according to the invention. Referring to FIG. 3, the acoustic calibration device 1 includes an upper chamber 31 connected to a lower chamber 33 by means of a neck 35 disposed therebetween. Media particles 37 (e.g., marbles, balls, beads, etc.) are stored in the upper chamber 31 and can flow through the neck 35 to the lower chamber 33 in a controlled fashion. The neck 35 also allows the passage of the media particles 37 from the lower chamber 31 to the upper chamber 33 if the device 1 is placed upside down. An impingement post 39, such as a sounding plate or a bell, is cantilevered in the lower chamber 33 by connecting one end of the impingement post 39 to the sidewall of the lower chamber 33. The impingement post 39 is placed generally horizontally and directly below the neck 35 in the lower chamber 33. The impingement post 39 can also be positioned in the upper chamber 31, or in both chambers 31 and 33 in other embodiments according to the invention which are further described below.

The acoustic calibration device 1 generates reproducible and repeatable sounds by allowing media particles 37 to fall through the neck 35 from the upper chamber 31 to the lower chamber 33 and onto the impingement post 39. A reverberating sound is generated when one of the media particles 37 contacts the impingement post 39. The media particles 37 are pre-sorted or control manufactured to have identical weight and sizes (within a margin of error) so that the sounds generated by the device 1 are consistently uniform for calibration purposes because the distance from neck 35 to post 39 is fixed. The device 1 can be used for ultrasonic calibration in both the airborne mode (ultrasound received in a gaseous medium) and the structure-borne mode (ultrasound received in a solid medium).

The device 1 according to the invention is a hermetically sealed unit, so that moisture will not enter into the upper and lower chambers 31 and 33, which could cause a non-uniform distribution of the media particles 37. The device 1 is generally in a hollow, tubular form, having any suitable length. The outer surface of device 1 may have any cross sectional shape, such as circular, as well as various polygonal shapes, including triangular, square, pentagonal, hexagonal, octagonal, etc. In the present embodiment of the invention, the device 1 is made by injection molding, so that unit-to-unit uniformity is maintained.

Figure 4B:
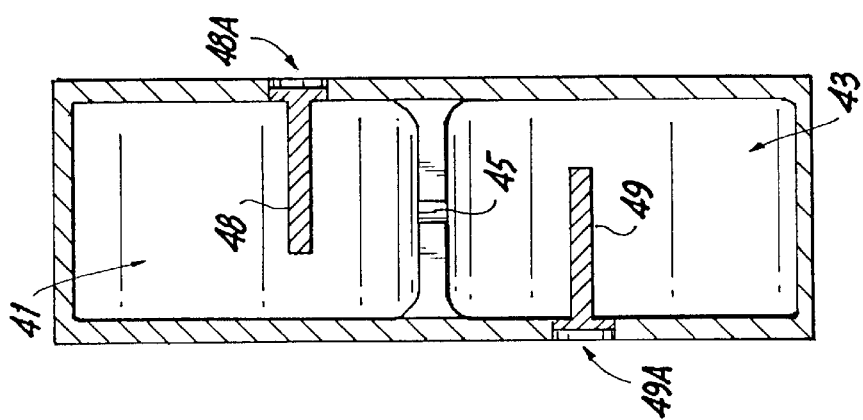
FIG. 4B is a cross sectional view of the device 24 FIG. 4A along line 4—4 thereof.
Figure 4A:
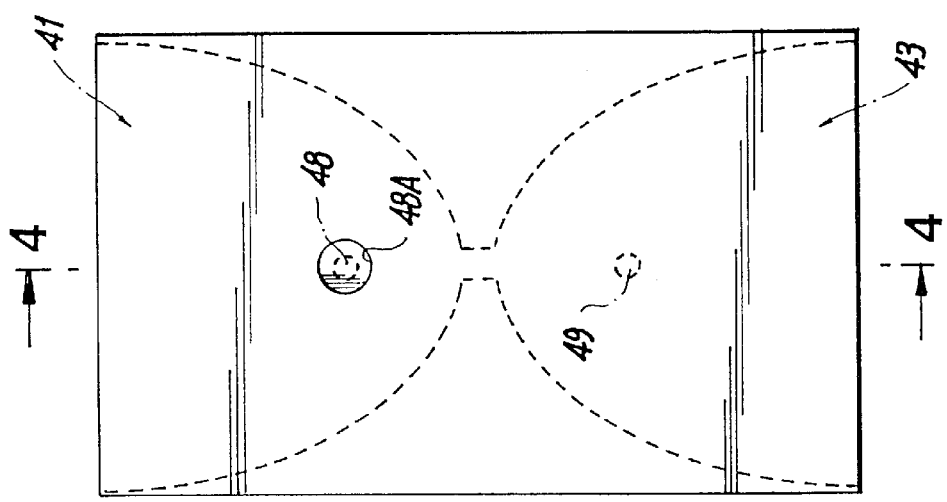
FIG. 4A is side elevation of another embodiment of the acoustic calibration device according to the invention.

FIGS. 4A and 4B are diagrams that illustrate a further embodiment of the acoustic calibration according to the invention. FIG. 4B is a cross sectional view taken along line 4—4 of the elevation view of the acoustic calibration device shown in FIG. 4A. Referring to FIGS. 4A and 4B, the acoustic calibration device includes an upper chamber 41 connected to a lower chamber 43 by an orifice 45 disposed therebetween. The orifice 45 permits the controlled passage of single media particles (not shown) from the upper chamber 41 to the lower chamber 43. When the acoustic calibration device is placed upside down, the orifice 45 similarly permits, due to gravity, the passage of media particles from the lower chamber 43 to the upper chamber 41 one at a time. The impingement posts 48 and 49 are respectively placed generally horizontally in the upper and lower chambers 41 and 43. The impingement posts 48 and 49, e.g., a bell post or a sounding plate, are respectively fastened to the acoustic calibration device at indent 48A and 49A.

Figure 5A:
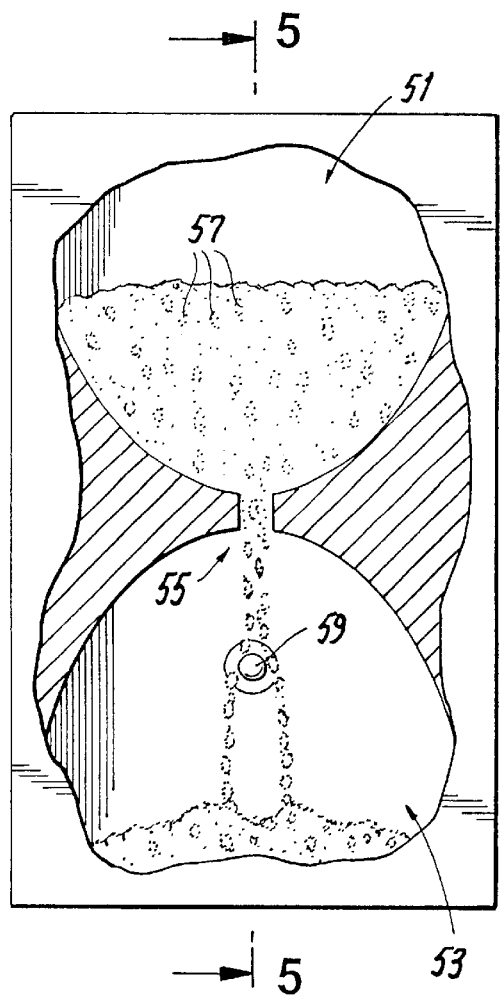
FIGS. 5A and 5B are respective views illustrating the embodiment of the invention as shown in FIGS. 4A and 4B with exemplary media particles, with FIG. 5B being a cross-sectional view along line 5—5 of the elevation view of FIG. 5A.
Figure 5B:
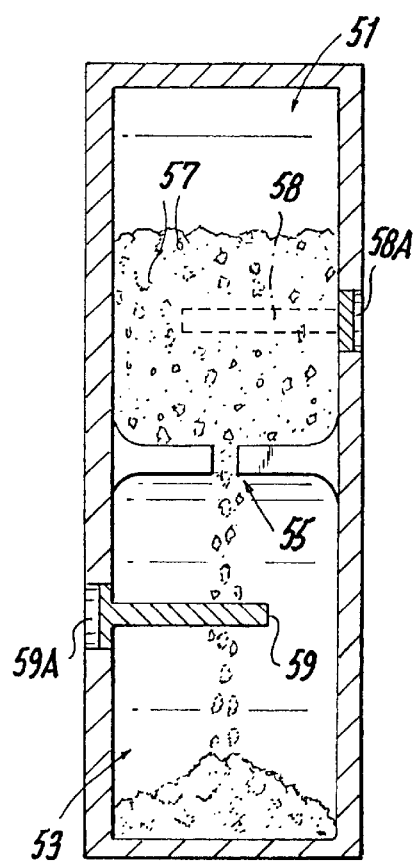

FIGS. 5A and 5B are diagrams that illustrate the embodiment of the invention (as shown in FIGS. 4A and 4B) with exemplary media particles. FIG. 5B is a cross-sectional view of the elevation view of the acoustic calibration device along line 5—5 and shown in FIG. 5A. The calibration device shown in FIGS. 5A and 5B have similar structural components as that of FIGS. 4A and 4B. Media particles 57 are found in the upper and lower chambers 51 and 53. The acoustic calibration device according to the invention generates reproducible and repeatable sounds since the orifice 55 only allows the media particles 57 to fall through the orifice 55 in a controlled fashion from the upper chamber 51 to the lower chamber 53 at a uniform rate. A reverberating sound is generated upon one of the media particles 37 contacting the impingement post 59.

Figure 1:
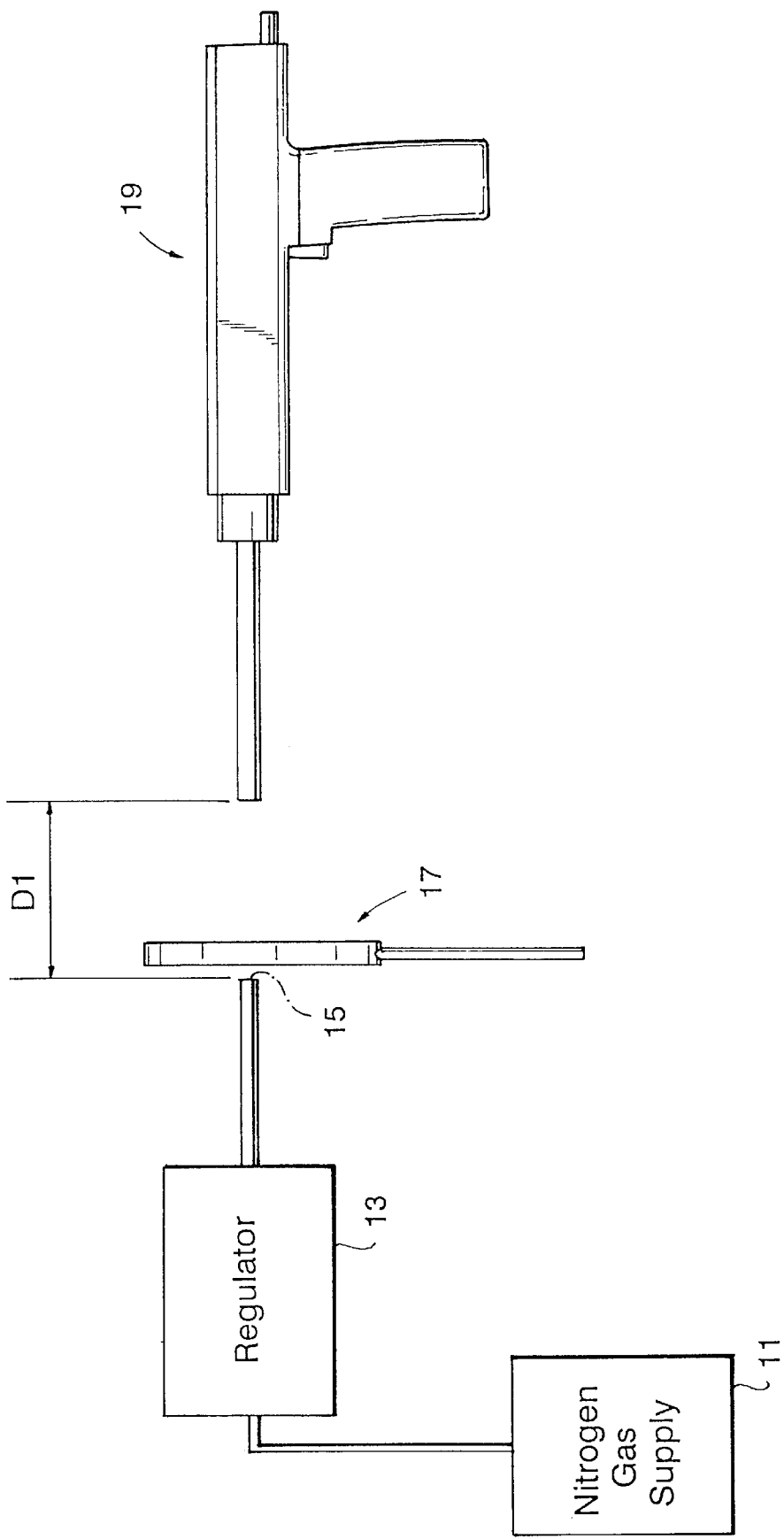
FIG. 1 is a diagram generally illustrating the equipment for a prior art calibration method for devices that detect gas leakage in the airborne mode.
Figure 2:
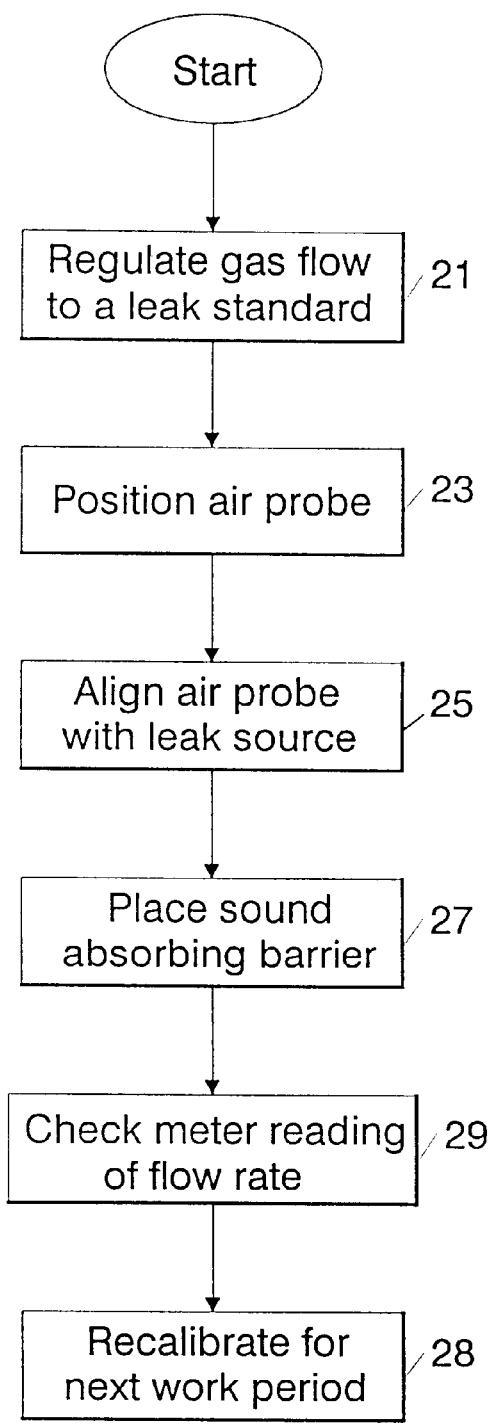
FIG. 2 is a flow diagram illustrating the operation of the calibration equipment shown in FIG. 1.
Figure 6:
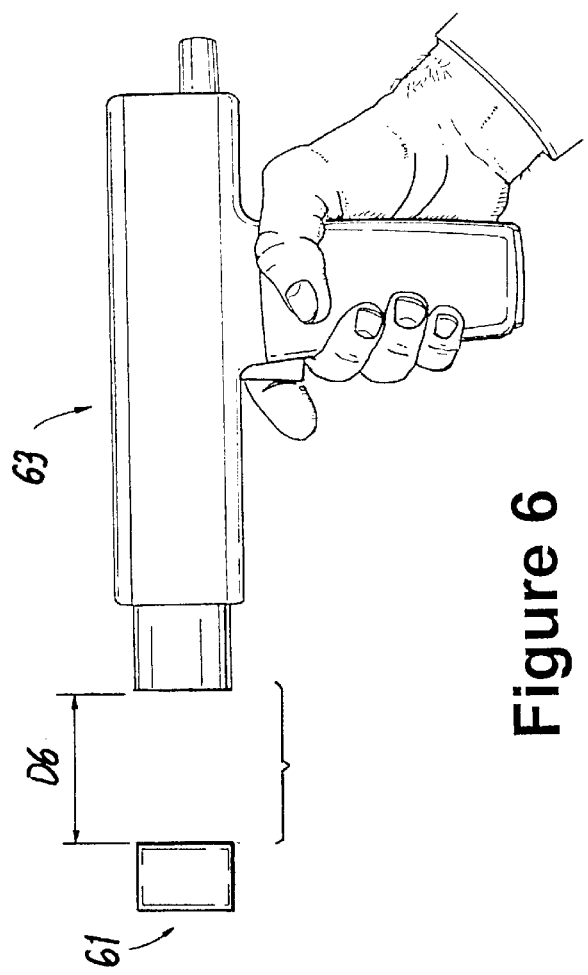
FIG. 6 is a diagram illustrating the operation of an acoustic calibration device according to the invention in the airborne mode.
Figure 7:
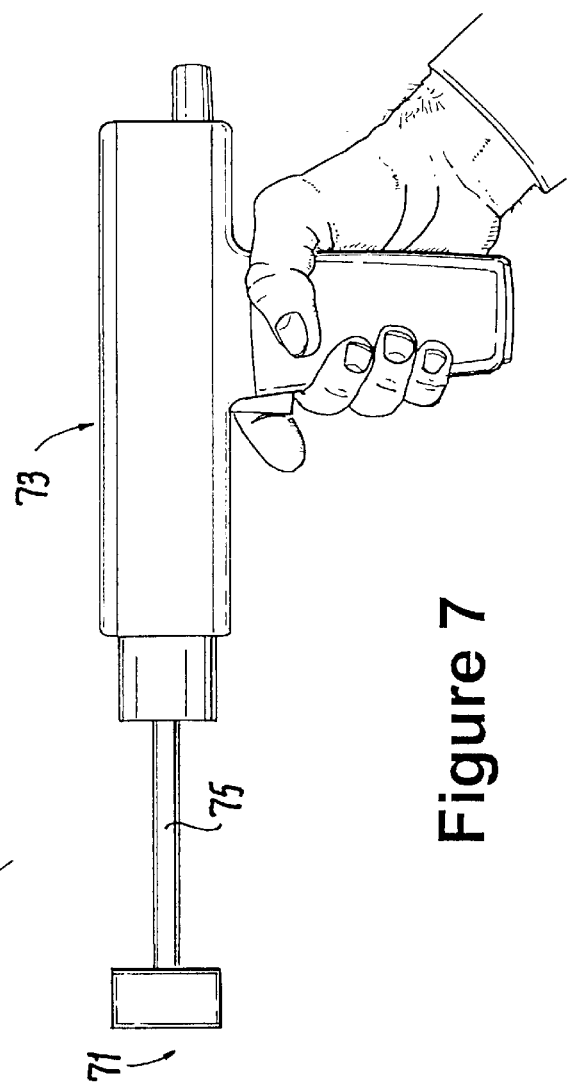
FIG. 7 is a diagram illustrating the operation of an acoustic calibration device according to the invention in the structure-borne mode.

The consistent, repeatable sounds generated by the acoustic calibration device according to the invention can be used as the standard for ultrasonic calibration in both the airborne mode and the structure-borne mode. FIGS. 6 and 7 are diagrams illustrating the operation of an acoustic calibration device according to the invention in the airborne mode and the structure-borne mode, respectively. Referring to FIG. 6, a probe 63 is placed at a short distance D6 (e.g., D6=5 cm) away from an acoustic calibration device 61 according to the invention. In contrast to conventional acoustic calibration devices, e.g., the calibration equipment shown in FIG. 1, the acoustic calibration device according to the invention advantageously occupies little space and is simple to use, without requiring cumbersome equipment and complex operating procedures. The probe 63 can be any acoustic or detection probe available in the art, e.g., ULTRAPROBE® 9000, ULTRAPROBE® 2000, ULTRAPROBE® 550, or ULTRA-PROBE® 100, all of which are available from UE Systems, Inc., the assignee of the invention. The consistent, repeatable sounds generated by the device 61 according to the principles of the invention described herein provide the standard for acoustically calibrating and testing the detection consistency of the probe 63.

Figure 8:
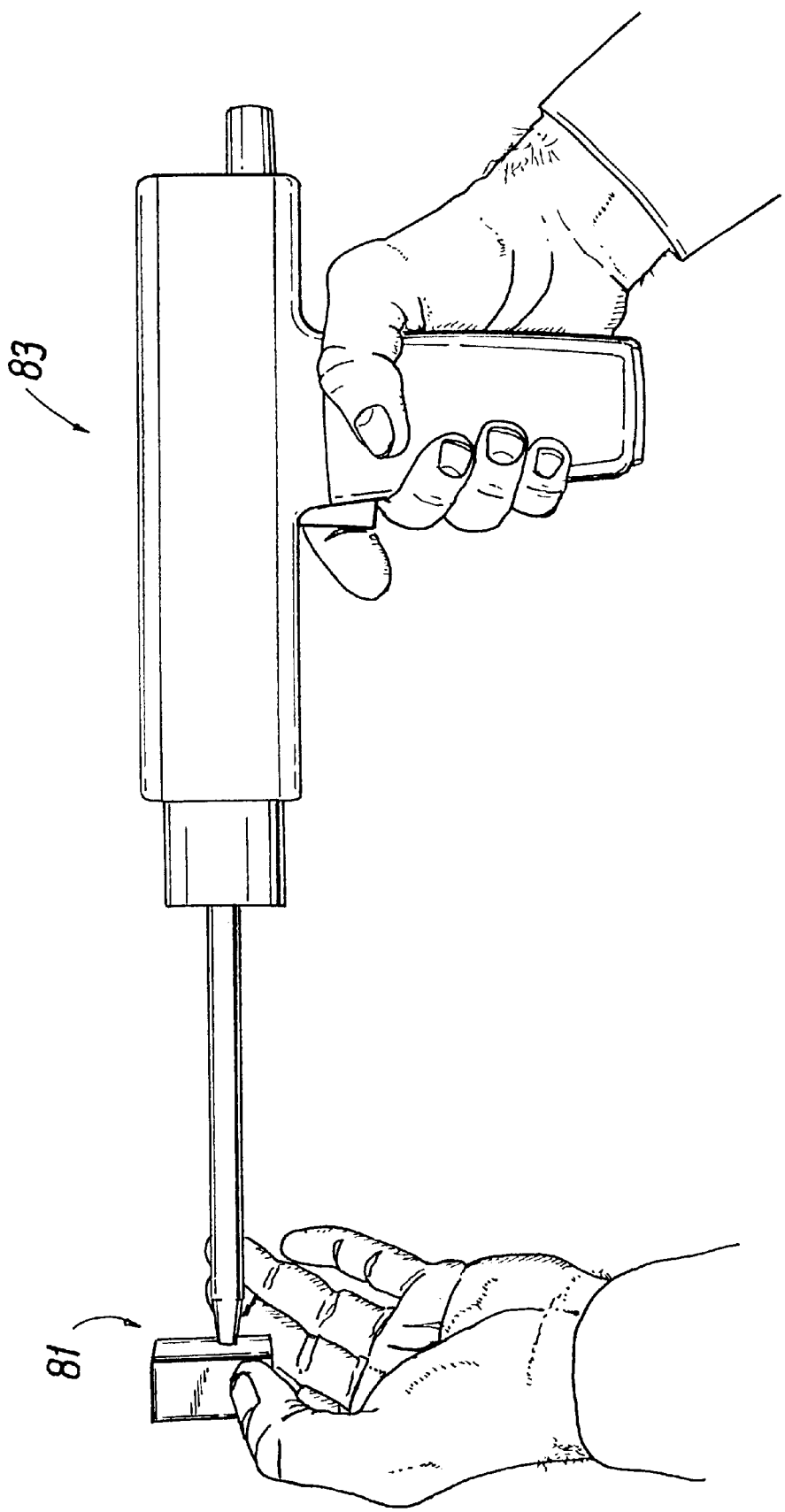
FIG. 8 is a diagram illustrating the operation of an acoustic calibration device according to the invention with an exemplary probe in the structure-borne mode.

Referring to FIG. 7, the acoustic calibration device 71 according to the invention can also be used for calibration in the structure-borne mode. The device 71 is fastened on the tip or spout 75 of the probe 73, which can be any acoustic or detection probe in the art, e.g., the ULTRAPROBE® series available from the assignee of the invention, as described herein. Probe 73 is used to detect ultrasonic vibrating or acoustic activity in the structure-borne mode, e.g., by contacting the detection tip or spout 75 of probe 73 with the solid medium to be tested. The consistent, repeatable sounds generated by device 71 according to the invention serve as the standard for acoustically calibrating the probe 73. An illustration of such an operation of the device 71 in acoustically calibrating a probe in the structure-borne mode is shown in FIG. 8. Structure-borne ultrasounds are microscopic oscillations or transverse waves in a structure that produce sound. Referring to FIG. 8, the acoustic calibration device 81 generates repeatable sounds which serve as the standard for acoustically calibrating and testing the detection consistency of an acoustic or detection probe 83.

The acoustic calibration device according to the invention can be used in acoustically calibrating and testing the detection consistency of acoustic or detection probes in many applications in the structure-borne mode and airborne modes. Structure-borne applications of the invention include, e.g., acoustic or vibration detection in mechanical bearings, gear boxes, line blockage, steam traps, valves, compressors, motors, pipes, flow direction, underground leaks, etc. Airborne applications of the invention include, e.g., vacuum leaks, as well as leaks in welds, substations, heat exchangers, seals, pumps, tanks, air brakes, gaskets and pressure leaks of all types, electric arc, caulking, air infiltration, wind noise, junction boxes, etc.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve substantially the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

We claim:

1. An ultrasonic acoustic calibration device, comprising:
   a plurality of media particles;
   an upper chamber, a lower chamber and a neck disposed therebetween for connecting said upper and lower chambers, said media particles being located in at least one of said chambers, said neck allowing controlled passage of the media particles due to gravity; and
   an impingement post disposed within at least one of said upper chamber and the lower chamber so as to be contacted by a media particle pulling through said neck such that a sound results when one of the media particles makes contact with the impingement post
   wherein the resulting sounds from the plurality of media particles making contact with the impingement post are reproducible and repeatable sounds used as a standard for ultrasonic calibration.

2. The device of claim 1, wherein the media particles are the same size and weight within a margin of error.

3. The device of claim 1, wherein the impingement post is cantilevered from a side wall of one of said chambers and is placed generally horizontally and below the neck.

4. The device of claim 1, whereas the impingement post comprises a bell or sounding plate.

5. The device of claim 1, wherein the device is used in ultrasonic calibration in one of the group consisting of an airborne mode and a structure-borne mode ultrasonic probe.

6. The device of claim 1, wherein the device is a hermetically sealed unit.

7. The device of claim 1, wherein the media particles are selected from the group of balls, marbles and beads.

8. The device of claim 1 wherein the device is used for acoustic calibration of a probe for measuring ultrasonic signals from at least one of mechanical bearings, gear boxes, line blockages, steam traps, valves, compressors, motors, pipes, flow direction controls, underground leaks, welds, vacuum leaks, substations, heat exchangers, seals, pumps, tanks, air brakes, gaskets, pressure leaks, electric arcs, caulking, air infiltration, wind noise, and junction boxes.

* * * * *